United States Patent
Liu et al.

(10) Patent No.: US 12,036,538 B2
(45) Date of Patent: Jul. 16, 2024

(54) MOLECULAR SIEVE CATALYST, PREPARATION METHOD THEREFOR, AND APPLICATION THEREOF

(71) Applicant: DALIAN INSTITUTE OF CHEMICAL PHYSICS, CHINESE ACADEMY OF SCIENCES, Liaoning (CN)

(72) Inventors: Hongchao Liu, Liaoning (CN); Shiping Liu, Liaoning (CN); Wenliang Zhu, Liaoning (CN); Zhongmin Liu, Liaoning (CN); Xiangang Ma, Liaoning (CN); Yong Liu, Liaoning (CN); Ziqiao Zhou, Liaoning (CN); Youming Ni, Liaoning (CN)

(73) Assignee: DALIAN INSTITUTE OF CHEMICAL PHYSICS, CHINESE ACADEMY OF SCIENCES, Liaoning (CN)

(*) Notice: Subject to any disclaimer, the term of this patent is extended or adjusted under 35 U.S.C. 154(b) by 427 days.

(21) Appl. No.: 17/426,979

(22) PCT Filed: Feb. 2, 2019

(86) PCT No.: PCT/CN2019/074590
§ 371 (c)(1),
(2) Date: Jul. 29, 2021

(87) PCT Pub. No.: WO2020/155144
PCT Pub. Date: Aug. 6, 2020

(65) Prior Publication Data
US 2022/0097032 A1   Mar. 31, 2022

(51) Int. Cl.
*B01J 29/18* (2006.01)
*B01J 6/00* (2006.01)

(52) U.S. Cl.
CPC .............. *B01J 29/18* (2013.01); *B01J 6/001* (2013.01); *B01J 2229/16* (2013.01); *B01J 2229/37* (2013.01); *B01J 2229/38* (2013.01)

(58) Field of Classification Search
CPC .... B01J 29/18; B01J 2229/16; B01J 2229/36; B01J 2229/37; B01J 37/22; B01J 37/24; B01J 37/26; B01J 37/30; B01J 37/10; B01J 37/08; C07C 67/37; C07C 69/14
USPC ............................................... 502/60, 62, 78
See application file for complete search history.

(56) References Cited

U.S. PATENT DOCUMENTS

| | | | |
|---|---|---|---|
| 7,465,822 | B2 | 12/2008 | Cheung et al. |
| 2018/0311654 | A1 | 11/2018 | Bae et al. |

FOREIGN PATENT DOCUMENTS

| | | |
|---|---|---|
| CN | 101613274 A | 12/2009 |
| CN | 101722034 A | 6/2010 |
| CN | 103121686 A | 5/2013 |
| CN | 105618112 A | 6/2016 |
| CN | 105669453 A | 6/2016 |
| EP | 2174713 A1 | 4/2010 |

OTHER PUBLICATIONS

Degin et al., MT CN 103 121 686, 2013, 10 pages.*
Lusardi, et al., "Carbonylation of Dimethyl Ether to Methyl Acetate over SSZ-13", ACS Catalysis, Dec. 2019.
Search Report dated Dec. 20, 2021 issued in corresponding European Application No. 19913504.7.
Search Report dated Oct. 25, 2019 issued in corresponding International Application No. PCT/CN2019/074590.
Office Action dated Dec. 11, 2020 issued in corresponding Chinese Application No. 201910107338.X.

* cited by examiner

*Primary Examiner* — Elizabeth D Wood
(74) *Attorney, Agent, or Firm* — Nath, Goldberg & Meyer; Joshua B. Goldberg; Leia Dingott

(57) ABSTRACT

Provided are a molecular sieve catalyst, a preparation method therefor, an application thereof. The molecular sieve catalyst contains a modified Na-MOR molecular sieve, and the modification comprises: organic ammonium salt exchange, dealumination treatment, and ammonium ion exchange. The catalyst obtained by the method is used in dimethyl ether for one-step production of methyl acetate. The catalyst has high activity and stable performance, and the needs of industrial production can be satisfied.

16 Claims, No Drawings

MOLECULAR SIEVE CATALYST, PREPARATION METHOD THEREFOR, AND APPLICATION THEREOF

This is a National Phase Application filed under 35 U.S.C. 371 as a national stage of PCT/CN2019/074590, filed Feb. 2, 2019, the content of which is hereby incorporated by reference in its entirety.

FIELD

The present application relates to a molecular sieve catalyst, a preparation method therefor and application thereof, and belongs to catalysis field.

BACKGROUND

With the rapid development of modern industry, the contradiction between energy supply and demand has become increasingly prominent. As a major energy-consuming country and also a major energy shortage country, it urgently needs to find alternative energy sources. As a clean energy, ethanol has good miscibility. It can be blended into gasoline as a blending component to partially replace gasoline, increase the octane number and oxygen content of gasoline, effectively promote the full combustion of gasoline, and reduce carbon monoxide and hydrocarbon emissions in automobile exhaust. Ethanol, as a partial substitute for vehicle fuel, can make our country's vehicle fuel present a diversified structural feature. At present, our country mainly uses grain, especially corn, to develop fuel ethanol. Thus, our country has become the third largest fuel ethanol producer and consumer after Brazil and the United States. However, according to our country's national conditions, there are many disadvantages in ethanol production using grain as raw material. The future more development of our country's fuel ethanol will be non-food routes.

Starting from coal resources, the production of ethanol from syngas is an important direction for the development of our country's new coal chemical industry and has broad market prospects. This has important strategic significance and far-reaching impact on the clean utilization of coal resources, alleviating the contradiction of the shortage of oil resources and improving our country's energy security. At present, the process route of coal-to-ethanol is mainly divided into two types: one is the direct production of ethanol from syngas; however, in such process route, a noble metal rhodium catalyst is required, the catalyst cost is high and the output of rhodium is limited. The other is syngas to ethanol via the hydrogenation of acetic acid, in which the syngas is first subjected to liquid phase carbonylation of methanol to produce acetic acid, and then hydrogenated to synthesize ethanol. The latter route is mature, but it requires equipment with special alloys that resist corrosion, and the cost is relatively high.

US20070238897A1 discloses that molecular sieves with 8-membered ring channel, such as MOR, FER, and OFF, are used as catalyst of carbonylation of ethers, wherein the size of the 8-membered ring channel is greater than 0.25×0.36 nm. Under the condition that mordenite is used as a catalyst, the temperature is 165° C., and the reaction pressure is 1 MPa, a space-time yield of $0.163\text{-MeOAc}(\text{g-Cat}\cdot\text{h})^{-1}$ is obtained. WO2008132450A1 discloses that copper and silver modified MOR catalysts have significantly better performance than unmodified MOR catalysts under hydrogen atmosphere at a temperature ranging from 250 to 350° C. CN102950018A discloses results of the carbonylation of dimethyl ether on the rare earth-containing ZSM-35/MOR eutectic molecular sieve. The results show that both the activity and stability of the eutectic molecular sieve as catalyst are significantly better than single ZSM-35, and the stability of the eutectic molecular sieve is significantly better than single MOR.

CN101613274A uses pyridine-based organic amines to modify the mordenite molecular sieve catalyst, and finds that the modification of the molecular sieve can significantly improve the stability of the catalyst. The conversion rate of dimethyl ether ranges from 10% to 60%, the selectivity of methyl acetate is greater than 99%, and the catalyst activity remains stable after 48 hours of reaction. The above-mentioned applications disclose a large number of research results of carbonylation of dimethyl ether, and catalysts used therein are mainly refer to molecular sieve with 8-membered ring channel such as MOR and FER. In the publicly reported results, the catalyst runs stably for less than 100 hours and is extremely easy to deactivate, and the relevant results cannot meet the needs of industrial production.

SUMMARY

According to one aspect of the present application, a molecular sieve catalyst is provided, which has high activity and stable performance and can meet the requirements of industrial production.

The present application provides a catalyst for carbonylation of dimethyl ether to produce methyl acetate, a preparation method therefor and application thereof. The catalyst is prepared by subjecting Na-MOR molecular sieve (sodium-type mordenite molecular sieve) to an exchange treatment of tetraalkyl ammonium chloride and its derivatives, acid treatment and/or steam treatment, and further an exchange treatment of ammonium chloride and/or ammonium nitrate. The dimethyl ether and the feeding gas containing carbon monoxide are fed into a reactor loaded with a catalyst containing acidic molecular sieve which is subjected to selective control of active sites. Methyl acetate is produced under the condition that the reaction temperature ranges from 150 to 280° C., the reaction pressure ranges from 0.5 to 25.0 MPa, and the space velocity of dimethyl ether ranges from 0.2 to 4 h. The present application provides a catalyst with high activity and stable performance, which can meet the requirements of industrial production.

The molecular sieve catalyst is characterized by containing a modified Na-MOR molecular sieve; the modification comprises: organic ammonium salt exchange, dealumination treatment and ammonium ion exchange.

Optionally, the dealumination treatment is selective dealumination (i.e., directional dealumination of molecular sieve).

Optionally, the modified Na-MOR molecular sieve is active component.

Optionally, calcination is performed after the ammonium ion exchange.

Optionally, the modification comprises successively organic ammonium salt exchange, dealumination treatment and ammonium ion exchange.

Optionally, the modification comprises successively organic ammonium salt exchange, acid treatment and/or steam treatment, and ammonium ion exchange.

Optionally, the modification comprises successively organic ammonium salt exchange, acid treatment, steam treatment, and ammonium ion exchange.

Optionally, the organic ammonium salt is at least one of alkyl ammonium chloride salt and alkyl ammonium nitrate salt.

Optionally, the molecular sieve catalyst is a modified Na-MOR molecular sieve.

Optionally, the organic ammonium salt exchange is an alkyl ammonium halide salt exchange.

Optionally, the molecular sieve catalyst is a modified Na-MOR molecular sieve; and the modification refers to alkyl ammonium chloride salt exchange, acid treatment and/or steam treatment, and ammonium nitrate exchange.

Optionally, the modification comprises successively alkyl ammonium chloride salt exchange, acid treatment and/or steam treatment, and ammonium nitrate exchange.

Optionally, the modification comprises successively alkyl ammonium chloride salt exchange, acid treatment, steam treatment, and ammonium nitrate exchange.

Optionally, the alkyl ammonium halide salt is at least one of compounds having a chemical formula shown in Formula I:

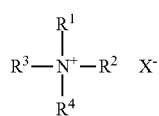

Formula I wherein $R^1$, $R^2$ and $R^3$ are independently selected from $C_1 \sim C_{10}$ alkyl group;

$R^4$ is selected from one of $C_1$ to $C_{10}$ alkyl group and $C_6$ to $C_{10}$ aryl group;

X is selected from at least one of F, Cl, Br and I.

Optionally, X is selected from one of F, Cl, Br and I.

Optionally, $R^1$, $R^2$ and $R^3$ are independently selected from $C_1 \sim C_6$ alkyl group.

Optionally, $R^1$, $R^2$ and $R^3$ are independently selected from $C_1 \sim C_4$ alkyl group.

Optionally, $R^1$, $R^2$ and $R^3$ are the same group.

Optionally, $R^1$, $R^2$ and $R^3$ are different groups.

Optionally, $R^4$ is selected from $C_6$ to $C_8$ aryl group.

Optionally, $R^4$ is selected from $C_6$ to $C_8$ alkyl-substituted benzene group.

Optionally, the alkyl ammonium halide salt is alkyl ammonium chloride salt.

Optionally, $R^1$, $R^2$, and $R^3$ in Formula I are independently selected from one of $CH_3-$, $CH_3CH_2-$, $CH_3(CH_2)_nCH_2-$, $(CH_3)_2CH-$, $(CH_3)_2CHCH_2-$, and $CH_3CH_2(CH_3)CH-$; and $R^4$ is one of $CH_3-$, $CH_3-$, $CH_3CH_2-$, $CH_3(CH_2)_mCH_2-$, $(CH_3)_2CH-$, $(CH_3)_2CHCH_2-$, $CH_3CH_2(CH_3)CH-$, $C_6H_5-$, $CH_3C_6H_4-$, $(CH_3)_2C_6H_3-$ and $C_6H_5CH_2-$; wherein, n and m are independently selected from 1, 2, 3 or 4.

Optionally, the silicon to aluminum atomic ratio of the Na-MOR molecular sieve ranges from 6 to 50.

Optionally, the upper limit of silicon to aluminum atomic ratio of the Na-MOR molecular sieve is 6.5, 10, 15, 20, 30, 40 or 50, and the lower limit thereof is 6, 6.5, 10, 15, 20, 30 or 40.

Optionally, the dealumination treatment comprises at least one of high-temperature calcination treatment and acid treatment.

Optionally, the high-temperature calcination treatment refers to calcination in an atmosphere with a steam concentration ranging from 0% to 100%.

Optionally, the atmosphere with a steam concentration ranging from 0 to 100% comprises steam, atmosphere A, a mixed atmosphere of steam and atmosphere A; wherein, the atmosphere A is at least one of air, nitrogen, and argon atmosphere.

As an embodiment, the catalyst for the carbonylation of dimethyl ether to produce methyl acetate comprises H-MOR molecular sieve as active component which is prepared by successively subjecting a Na-MOR molecular sieve to $(R^1)(R^2)(R^3)(R^4)NCl$ (i.e., alkyl ammonium chloride salt) exchange, acid treatment and/or steam treatment, which can provide a new catalyst system for producing methyl acetate from dimethyl ether.

Optionally, the catalyst is prepared by $(R^1)(R^2)(R^3)(R^4)NCl$ (i.e., alkyl ammonium chloride salt) exchange, acid treatment and/or steam treatment.

According to another aspect of the present application, a method for preparing the molecular sieve catalyst is provided, which is characterized by comprising subjecting the Na-MOR molecular sieve to organic ammonium salt exchange, dealumination treatment, ammonium ion exchange, and calcination to obtain the molecular sieve catalyst.

Optionally, the method for preparing the molecular sieve catalyst comprises following steps:
(1) subjecting Na-MOR molecular sieve to organic ammonium salt exchange to obtain a precursor I;
(2) subjecting the precursor I to the acid treatment to obtain a precursor II;
(3) subjecting the precursor II to a high-temperature calcination treatment to obtain a precursor III;
(4) subjecting the precursor III to an ammonium ion exchange to obtain a precursor IV; and
(5) calcining the precursor IV to obtain the molecular sieve catalyst.

Optionally, the conditions for the organic ammonium salt exchange in step (1) are the followings: Na-MOR molecular sieve is placed in an organic ammonium salt solution at a temperature ranging 20 to 100° C. for a time ranging from 1 to 10 hours.

Optionally, the upper limit of temperature of the organic ammonium salt exchange is 30° C., 40° C., 50° C., 60° C., 70° C., 80° C., 90° C. or 100° C., and the lower limit of temperature thereof is 20° C., 30° C., 40° C., 50° C., 60° C., 70° C., 80° C. or 90° C.

Optionally, the upper limit of time of the organic ammonium salt exchange is 2 hours, 3 hours, 4 hours, 5 hours, 6 hours, 7 hours, 8 hours, 9 hours or 10 hours.

Optionally, the concentration of the organic ammonium salt solution ranges from 0.05 to 1 mol/L.

Optionally, the ratio of the Na-MOR molecular sieve to the organic ammonium salt solution by volume ranges from 1:1 to 1:15 (g/ml).

Optionally, the solid-liquid ratio in the organic ammonium salt exchange ranges from 1 g:2 mL to 1 g: 15 mL.

Optionally, the upper limit of the concentration of the organic ammonium salt solution is 0.08 mol/L, 0.1 mol/L, 0.3 mol/L, 0.5 mol/L, 0.8 mol/L or 1 mol/L; and the lower limit thereof is 0.05 mol/L, 0.08 mol/L, 0.1 mol/L, 0.3 mol/L, 0.5 mol/L or 0.8 mol/L.

Optionally, the number of times the organic ammonium salt exchange ranges from 2 to 8; and the conditions for the organic ammonium salt exchange refers to a temperature ranging from 30 to 80° C., and an exchange time ranging from 2 to 6 hours.

Optionally, the step (1) comprises: subjecting a sample containing Na-MOR to an exchange treatment in organic ammonium salt solution at a temperature ranging from 20 to 100° C. for a time ranging from 1 to 10 hours, then washing, filtering, and drying the product; repeating the above step (1) 2 to 8 times.

Optionally, the acid used in the acid treatment in step (2) is at least one of hydrochloric acid, nitric acid, sulfuric acid, acetic acid, oxalic acid and citric acid.

Optionally, the acid treatment in step (2) is carried out in an acidic solution at a temperature ranging 30 to 100° C. for a time ranging from 1 to 10 hours.

Optionally, the concentration of the acidic solution ranges from 0.05 to 1.5 mol/L.

Optionally, the upper limit of temperature of the acid treatment is 40° C., 50° C., 60° C., 80° C. or 100° C., and the lower limit thereof is 30° C., 40° C., 50° C., 60° C. or 80° C.

Optionally, the upper limit of the time of the acid treatment is 2 hours, 3 hours, 5 hours, 8 hours or 10 hours, and the lower limit thereof is 1 hour, 2 hour, 3 hours, 5 hours or 8 hours.

Optionally, the number of times the acid treatment ranges from 2 to 10; and the acid treatment is carried out in an acidic solution at a temperature ranging 30 to 80° C. for a time ranging from 2 to 8 hours.

Optionally, the step (2) comprises treating the persecutor obtained in step (1) with an acidic solution at a temperature ranging from 30 to 100° C. for a time ranging from 1 to 10 hours, then washing, filtering, and drying the product; repeating the above steps 2 to 10 times.

Optionally, the high-temperature calcination treatment in step (3) is carried out in an atmosphere with a steam concentration ranging from 0 to 100%, at a temperature ranging from 300 to 800° C. for a time ranging from 1 to 10 hours.

Optionally, the upper limit of the steam concentration of the high-temperature calcination atmosphere is 10%, 20%, 30%, 40%, 50%, 60%, 70%, 80%, 90% or 100%; and the lower limit thereof is 0%, 10%, 20%, 30%, 40%, 50%, 60%, 70%, 80% or 90%.

Optionally, the upper limit of the temperature of the high-temperature calcination treatment is 350° C., 400° C., 450° C., 500° C., 550° C., 600° C., 650° C., 700° C., 750° C. or 800° C., and the lower limit thereof is 300° C., 350° C., 400° C., 450° C., 500° C., 550° C., 600° C., 650° C., 700° C. or 750° C.

Optionally, the upper limit of the time of the high-temperature calcination treatment is 2 hours, 3 hours, 4 hours, 5 hours, 6 hours, 7 hours, 8 hours, 9 hours or 10 hours; and the lower limit thereof is 1 hour, 2 hours, 3 hours, 4 hours, 5 hours, 6 hours, 7 hours, 8 hours or 9 hours.

Optionally, the high-temperature calcination treatment is carried out in an atmosphere with a steam concentration ranging from 0% to 100% at a temperature ranging from 350 to 750° C. for a time ranging from 2 to 6 hours.

Optionally, the step (3) comprises treating the persecutor obtained in step (2) in an atmosphere with a steam concentration ranging from 0 to 100% at a temperature ranging from 300 to 800° C. for a time ranging from 1 to 10 hours.

Optionally, the ammonium ion exchange in step (4) is carried out at a temperature ranging from 20 to 100° C. for a time ranging from 1 to 10 hours.

Optionally, the upper limit of the temperature of the ammonium ion exchange is 30° C., 40° C., 50° C., 60° C., 70° C., 80° C., 90° C. or 100° C.; and the lower limit thereof is 20° C., 30° C., 40° C., 50° C., 60° C., 70° C., 80° C. or 90° C.

Optionally, the upper limit of the time of the ammonium ion exchange is 2 hours, 3 hours, 4 hours, 5 hours, 6 hours, 7 hours, 8 hours, 9 hours or 10 hours; and the lower limit thereof is 1 hour, 2 hours, 3 hours, 4 hours, 5 hours, 6 hours, 7 hours, 8 hours or 9 hours.

Optionally, the number of times the ammonium ion exchange is 2 to 5; the ammonium ion exchange is carried out at a temperature ranging from 30 to 90° C. for a time ranging from 2 to 6 hours;

The ammonium ion exchange is carried out in an ammonium ion-containing solution; and the ammonium ion-containing solution is at least one of ammonium nitrate solution, ammonium chloride solution, ammonium sulfate solution, and ammonium acetate solution.

Optionally, the step (4) comprises carrying out the ammonium ion-containing solution for the persecutor obtained in step (3) in the ammonium ion-containing solution at a temperature ranging from 20 to 100° C. for a time ranging from 1 to 10 hours, then washing, filtering, and drying the resulting product, and repeating the above step 2 to 5 times.

Optionally, the calcination in step (5) is carried out in an air atmosphere at a temperature ranging from 300 to 800° C. for a time ranging 2 to 8 hours.

Optionally, the upper limit of a calcination temperature is 350° C., 400° C., 450° C., 500° C., 550° C., 600° C., 650° C., 700° C., 750° C. or 800° C.; and the lower limit thereof is 300° C., 350° C., 400° C., 450° C., 500° C., 550° C., 600° C., 650° C., 700° C. or 750° C.

Optionally, the upper limit of a calcination time is 3 hours, 4 hours, 5 hours, 6 hours, 7 hours, or 8 hours; and the lower limit thereof is 2 hours, 3 hours, 4 hours, 5 hours, 6 hours or 7 hours.

Optionally, the calcination is carried out in an air atmosphere at a temperature ranging from 400 to 750° C. for a time ranging 4 to 6 hours.

Optionally, the step (5) comprising calcining the persecutor obtained in step (4) in an air atmosphere at a temperature ranging from 300 to 800° C. for a time ranging from 2 to 8 hours to obtain a catalyst.

Optionally, the method for preparing the molecular sieve catalyst comprises following steps:

a) subjecting a solid containing Na-MOR molecular sieve to an exchange treatment in a solution containing alkyl ammonium halide salt at a temperature ranging from 20 to 100° C. for a time ranging from 1 to 10 hours to obtain the precursor I, wherein the number of times the exchange treatment ranges from 2 to 8;

b) treating the precursor I with an acidic solution at a temperature ranging from 30 to 100° C. for a time ranging from 1 to 10 hours to obtain the precursor II, wherein the number of times the treatment with the acidic solution is 2 to 10 times;

c) treating the precursor II in an atmosphere with a steam concentration ranging from 0% to 100%, at a temperature ranging from 300 to 800° C. for a time ranging from 1 to 10 hours to obtain the precursor III;

d) subjecting the precursor III to an exchange treatment in an ammonium nitrate aqueous solution at a temperature ranging from 20 to 100° C. for a time ranging from 1 to 10 hours to obtain the precursor IV, wherein the number of times the exchange treatment ranges from 2 to 5 times;

e) calcining the precursor IV in an air atmosphere at a temperature ranging from 300 to 800° C. for a time ranging from 2 to 8 hours to obtain the molecular sieve catalyst.

As a specific embodiment, the method for preparing the molecular sieve catalyst comprises following steps:
- (S1) subjecting a sample containing Na-MOR to an exchange treatment in $(R_1)(R_2)(R_3)(R_4)NCl$ salt solution at a temperature ranging from 20 to 100° C. for a time ranging from 1 to 10 hours, then washing, filtering and drying the resulting product; and repeating the above step 2 to 8 times;
- (S2) treating the product obtained in step (S1) with an acidic solution at a temperature ranging from 30 to 100° C. for a time ranging from 1 to 10 hours, then washing, filtering, and drying the resulting product; and repeating the above step 2 to 10 times;
- (S3) treating the product obtained in step (S2) in a steam atmosphere at a temperature ranging from 300 to 800° C. for a time ranging from 1 to 10 hours;
- (S4) subjecting the product obtained in step (S3) to an exchange treatment in an ammonium nitrate aqueous solution at a temperature ranging from 20 to 100° C. for a time ranging from 1 to 10 hours, then washing, filtering and drying the resulting product; and repeating the above step 2 to 5 times; and
- (S5) calcining the product obtained in step (S4) in an air atmosphere at a temperature ranging from 300 to 800° C. for a time ranging from 2 to 8 hours to prepare the molecular sieve catalyst.

According to a further aspect of the present application, use of at least one of any one of molecular sieve catalyst described above and the molecular sieve catalyst prepared according to any one of methods described above in carbonylation of dimethyl ether to produce methyl acetate is provided.

According to another aspect of the present application, a method for producing methyl acetate by carbonylation of dimethyl ether is provided, which is characterized by comprising feeding dimethyl ether and a feeding gas containing carbon monoxide into a reactor equipped with a catalyst bed to contact with a catalyst to produce methyl acetate; wherein, the catalyst is at least one of any one of molecular sieve catalyst described above and the molecular sieve catalyst prepared according to any one of methods described above.

Those skilled in the art can select procedure conditions according to actual needs, such as a ratio of dimethyl ether to carbon monoxide in the feeding gas, reaction temperature, reaction pressure, and space velocity.

Those skilled in the art can select a suitable reactor according to actual production needs.

Optionally, the reaction conditions refer to the followings: the reaction temperature ranges from 150 to 280° C., the reaction pressure ranges from 0.5 to 25.0 MPa, the weight hourly space velocity of the feeding dimethyl ether ranges from 0.05 to 5 $h^{-1}$; and a molar ratio of carbon monoxide to dimethyl ether ranges from 0.1:1 to 30:1.

Optionally, the upper limit of the reaction temperature is 160° C., 170° C., 180° C., 200° C., 210° C., 220° C., 230° C., 240° C., 250° C., 260° C., 270° C. or 280° C.; and the lower limit thereof is 150° C., 160° C., 170° C., 180° C., 200° C., 210° C., 220° C., 230° C., 240° C., 250° C., 260° C. or 270° C.

Optionally, the upper limit of the reaction pressure is 1 MPa, 2 MPa, 5 MPa, 6 MPa, 8 MPa, 10 MPa, 12 MPa, 15 MPa, 18 MPa, 20 MPa or 25 MPa; and the lower limit thereof is 0.5 MPa, 1 MPa, 2 MPa, 5 MPa, 6 MPa, 8 MPa, 10 MPa, 12 MPa, 15 MPa, 18 MPa or 20 MPa.

Optionally, the weight hourly space velocity of the feeding dimethyl ether is 0.1 $h^{-1}$, 0.2 $h^{-1}$, 0.25 $h^{-1}$, 0.35 $h^{-1}$, 0.5 $h^{-1}$, 1 $h^{-1}$, 1.2 $h^{-1}$, 1.5 $h^{-1}$, 2 $h^{-1}$, 2.5 $h^{-1}$, 4 $h^{-1}$, 4.5 $h^{-1}$ or 5 $h^{-1}$; and the lower limit thereof is 0.05 $h^{-1}$, 0.1 $h^{-1}$, 0.2 $h^{-1}$, 0.25 $h^{-1}$, 0.35 $h^{-1}$, 0.5 $h^{-1}$, 1 $h^{-1}$, 1.2 $h^{-1}$, 1.5 $h^{-1}$, 2 $h^4$, 2.5 $h^{-1}$, 4 $h^{-1}$ or 4.5 $h^{-1}$.

Optionally, the upper limit of the molar ratio of carbon monoxide to dimethyl ether is 0.2:1, 0.5:1, 1:1, 2:1, 4:1, 6:1, 8:1, 12:1, 15:1, 18:1, 20:1, 25:1 or 30:1; and the lower limit thereof is 0.1:1, 0.2:1, 0.5:1, 1:1, 2:1, 4:1, 6:1, 8:1, 12:1, 15:1, 18:1, 20:1 or 25:1.

Optionally, the reaction conditions refer to the followings: the reaction temperature ranges from 160 to 280° C., the reaction pressure ranges from 0.5 to 20.0 MPa, and the weight hourly space velocity of the feeding dimethyl ether ranges from 0.2 to 4.0 $h^{-1}$, and the molar ratio of carbon monoxide to dimethyl ether ranges from 0.1:1 to 20:1.

Optionally, the reaction conditions refer to the followings: the reaction temperature ranges from 170 to 260° C., the reaction pressure ranges from 1.0 to 15.0 MPa, and the weight hourly space velocity of the feeding dimethyl ether ranges from 0.1 to 4.0 $h^{-1}$; and the molar ratio of carbon monoxide to dimethyl ether ranges from 0.2:1 to 15:1.

Optionally, the reaction conditions refer to the followings: the reaction temperature ranges from 160 to 280° C., the reaction pressure ranges from 0.5 to 20.0 MPa, the weight hourly space velocity of the feeding dimethyl ether ranges from 0.05 to 5 $h^{-1}$, and the molar ratio of carbon monoxide to dimethyl ether ranges from 0.1:1 to 20:1.

Optionally, the feeding gas containing carbon monoxide comprises from 15% to 100% carbon monoxide by volume.

Optionally, the feeding gas containing carbon monoxide further comprises inactive gas.

Optionally, the inactive gas is at least one of inert gas, hydrogen, nitrogen, carbon dioxide, methane and ethane.

Optionally, the feeding gas containing carbon monoxide further comprises at least one of hydrogen, nitrogen, helium, argon, carbon dioxide, methane and ethane.

Optionally, the feeding gas containing carbon monoxide further comprises from 0% to 85% other gas excluding carbon monoxide by volume.

Optionally, the reactor is a fixed bed reactor.

Optionally, the method for producing methyl acetate by carbonylation of dimethyl ether achieves greater than 90% selectivity of methyl acetate in the product.

Optionally, the method for producing methyl acetate by carbonylation of dimethyl ether achieves greater than 98% selectivity of methyl acetate in the product.

Optionally, the method for producing methyl acetate by carbonylation of dimethyl ether achieves a high space-time yield of methyl acetate in the product, which can reach ≥1 gMAc/(gcat·h).

In the present application, "$C_1 \sim C_{10}$", "$C_6$ to $C_{10}$" and the like all refer to the number of carbon atoms contained in the group.

In the present application, "aryl" is a group formed by the loss of any hydrogen atom on the molecule of an aromatic compound.

In the present application, "alkyl" is a group formed by the loss of any hydrogen atom on the molecule of an alkane compound.

The beneficial effects that the present application can achieve comprise:
1) The present application provides a catalyst for one-step production of methyl acetate from dimethyl ether. The catalyst has high activity and achieves high space-time yield of methyl acetate. The catalyst further high stable performance, and the lifetime thereof was greater than 8000 hours, thereby possessing a strong industrial application value.

2) The present application provides a method for preparing the catalyst, which can realize the directional elimination and protection of acid sites of the catalyst, and is a new method for preparing molecular sieve catalyst.

3) The catalyst of the present application is applied to the carbonylation of dimethyl ether to produce methyl acetate, which not only can ensure high product yield and long life, but also has a wide adjustable range of reaction process conditions, making the present invention possess universality and extremely wide application in industry.

DETAILED DESCRIPTION

The present application will be described in detail below with reference to the examples, but the present application is not limited to these examples.

Unless otherwise specified, the raw materials in the examples of the present application are all commercially available, wherein Na-MOR is purchased from Nankai University Catalyst Co., Ltd.

The analysis methods in the examples of the present application are as follows.

The gas after reaction is introduced into the online chromatograph through the heated pipeline for online analysis. The chromatograph is an Agilent 7890A equipped with a PLOT Q capillary column and a TDX-1 packed column, wherein the outlet of the PLOT-Q capillary column is connected to an FID detector, and the outlet of the TDX-1 packed column is connected to a TCD detector.

The conversion rate and selectivity in the examples of the present application are calculated as follows:

In the examples of the present application, the conversion rate of dimethyl ether, the conversion rate of carbon monoxide, and the selectivity of methyl acetate are calculated as below.

In the examples, the conversion rate of dimethyl ether and the selectivity of methyl acetate are both calculated based on the number of carbon moles of dimethyl ether.

Conversion rate of dimethyl ether=[(the molar number of carbon of dimethyl ether in raw materials)−(the molar number of carbon of dimethyl ether in the product)]÷(the molar number of carbon of dimethyl ether in the raw materials)×(100%)

Selectivity of methyl acetate=(⅔)×(the molar number of carbon of methyl acetate in the product)÷[(the molar number of carbon of dimethyl ether in the feeding gas)−(the molar number of carbon of dimethyl ether in the product)]×(100%)

Conversion rate of carbon monoxide=[(the molar number of CO before reaction)−(the molar number of CO after reaction)]÷(the molar number of CO before reaction)×(100%)

According to an embodiment of the present application, the catalyst for carbonylation of dimethyl ether to produce methyl acetate refers to the one containing H-MOR molecular sieve as an active component which is obtained by modification.

As an embodiment, the modified Na-MOR molecular sieve is prepared by successive $(R_1)(R_2)(R_3)(R_4)NCl$ (i.e., alkyl ammonium chloride salt) exchange, acid and/or steam treatment, and ammonium nitrate exchange.

As an embodiment, the silicon to aluminum atomic ratio of the Na-MOR molecular sieve ranges from 6 to 50.

As an embodiment, $R_1$, $R_2$ and $R_3$ in $(R_1)(R_2)(R_3)(R_4)NCl$ (i.e., alkyl ammonium chloride salt) are independently selected from one of $CH_3$—, $CH_3CH_2$—, $CH_3(CH_2)_nCH_2$— (wherein 0≤n≤4), $(CH_3)_2CH$—, $(CH_3)_2CHCH_2$—, and $CH_3CH_2(CH_3)$ CH—; and $R_4$ therein is one of $CH_3$—, $CH_3$—, $CH_3CH_2$—, $CH_3(CH_2)_nCH_2$— (wherein 0≤n≤4), $(CH_3)_2CH$—, $(CH_3)_2CHCH_2$—, $CH_3CH_2$ $(CH_3)CH$—, $C_6H_5$—, $CH_3C_6H_4$—, $(CH_3)_2C_6H_3$— and $C_6H_5CH_2$—.

As an embodiment, the $(R_1)(R_2)(R_3)(R_4)NCl$ salt is preferably one of tetramethyl ammonium chloride, tetraethyl ammonium chloride, tetrapropyl ammonium chloride, ethyl trimethyl ammonium chloride, diethyl dimethyl ammonium chloride, triethyl methyl ammonium chloride, phenyl trimethyl ammonium chloride, and benzyl trimethyl ammonium chloride, and any combination thereof.

As an embodiment, a method for preparing the catalyst for carbonylation of dimethyl ether to produce methyl acetate is characterized by comprising the following steps:
a) subjecting a sample containing Na-MOR to an exchange treatment in $(R_1)(R_2)(R_3)(R_4)NCl$ salt solution at a temperature ranging from 20 to 100° C. for a time ranging from 1 to 10 hours, then washing, filtering and drying the resulting product; and repeating the above step 2 to 8 times;
b) treating the product obtained in step a) with an acidic solution at a temperature ranging from 30 to 100° C. for a time ranging from 1 to 10 hours, then washing, filtering, and drying the resulting product; and repeating the above step 2 to 10 times;
c) treating the product obtained in step b) in a steam atmosphere at a temperature ranging from 300 to 800° C. for a time ranging from 1 to 10 hours;
d) subjecting the product obtained in step c) to an exchange treatment in an ammonium nitrate aqueous solution at a temperature ranging from 20 to 100° C. for a time ranging from 1 to 10 hours, then washing, filtering and drying the resulting product; and repeating the above step 2 to 5 times;
e) calcining the product obtained in step d) in an air atmosphere at a temperature ranging from 300 to 800° C. for a time ranging from 2 to 8 hours to obtain the catalyst.

As an embodiment, the concentration of the salt solution in step a) ranges from 0.05 to 1 mol/L.

As an embodiment, the temperature of the exchange treatment in step a) ranges from 30 to 80° C., and the time of the exchange treatment in step a) ranges from 2 to 6 hours.

As an embodiment, the acidic solution in step b) is one or more of hydrochloric acid, nitric acid, sulfuric acid, acetic acid, oxalic acid and citric acid.

As an embodiment, the temperature of the acid treatment in step b) ranges from 30 to 80° C., and the time of the acid treatment ranges from 2 to 8 hours.

As an embodiment, the step c) is carried out in the steam atmosphere at a temperature ranging from 350 to 750° C. for a time ranging from 2 to 6 hours.

As an embodiment, the step d) is carried out at a temperature ranging from 30 to 90° C. for a time ranging from 2 to 6 hours.

As an embodiment, the product obtained in step e) is calcined in an air atmosphere at a temperature ranging from 400 to 750° C. for a time ranging from 4 to 6 hours.

As an embodiment, the method for producing methyl acetate by carbonylation of dimethyl ether comprises: feeding dimethyl ether and a feeding gas containing carbon monoxide into a reactor to contact with the catalyst described in any one of the above or the catalyst for the carbonylation of dimethyl ether to produce methyl acetate prepared according to any one of methods mentioned above, to produce methyl acetate under the condition that the reaction temperature ranges from 150 to 280° C., the reaction pressure ranges from 0.5 to 25.0 MPa, and the space velocity of dimethyl ether ranges from 0.2 to 4 $h^{-1}$; and the molar ratio of dimethyl ether to carbon monoxide in the raw materials ranges from 0.1:1 to 30:1.

As an embodiment, the carbonylation is carried out under the condition that a reaction temperature ranges from 160 to 280° C., a reaction pressure ranges from 0.5 to 20.0 MPa, a weight hourly space velocity of the feeing dimethyl ether ranges from 0.05 to 5 $h^{-1}$, and the molar ratio of carbon monoxide to dimethyl ether ranges from 0.1:1 to 20:1.

As an embodiment, the reaction temperature ranges from 170 to 260° C., the reaction pressure ranges from 1.0 to 15.0 MPa, the weight hourly space velocity of the feeding dimethyl ether ranges from 0.1 to 4.0 $h^{-1}$, and the molar ratio of carbon monoxide to dimethyl ether ranges from 0.2:1 to 15:1.

As an embodiment, in addition to carbon monoxide, the feeding gas containing carbon monoxide may comprise any one or more of hydrogen, nitrogen, helium, argon, carbon dioxide, methane and ethane; preferably, based on the total volume content of the feeding gas containing carbon monoxide, the volume content of carbon monoxide ranges from 15% to 100%, and the volume content of other gases such as one or more of hydrogen, nitrogen, helium, argon, carbon dioxide, methane and ethane ranges from 0 to 85%.

Example 1

100 g Na-MOR (Si/Al=15) molecular sieve was added into 1000 mL 0.5 mol/L phenyltrimethylammonium chloride aqueous solution, and then was treated at 80° C. for 4 hours to undergo phenyltrimethylammonium chloride exchange treatment. After subsequent filtering, washing and drying steps, the above phenyltrimethylammonium chloride exchange process was repeated 5 times. Then, the resulting sample was added into 1000 mL 0.5 mol/L oxalic acid aqueous solution, and was treated at 60° C. for 3 hours to undergo acid treatment. After subsequent filtering, washing and drying steps, the above acid treatment process was repeated 3 times. Then, the resulting sample was treated in a dry air atmosphere at 650° C. for 4 hours to undergo the high temperature treatment. Then the sample obtained by the high temperature treatment was treated in 500 mL 1 mol/L ammonium nitrate aqueous solution at 70° C. for 4 hours to undergo ammonium nitrate solution exchange treatment. After washing and drying steps, the ammonium nitrate solution exchange treatment process was repeated 3 times. Then, the sample obtained finally was calcined at 550° C. for 4 hours in an air atmosphere to obtain 1 # catalyst.

Example 2

The phenyltrimethylammonium chloride was replaced with tetramethyl ammonium chloride, tetraethyl ammonium chloride, tetrapropyl ammonium chloride, ethyl trimethyl ammonium chloride, diethyl dimethyl ammonium chloride, triethyl methyl ammonium chloride, benzyl trimethyl ammonium chloride and a mixture of the described ammonium chloride salts with equal weight, respectively. All the rest preparation procedures are the same as those in Example 1 to correspondingly prepare 2 # catalyst, 3 # catalyst, 4 # catalyst, 5 # catalyst, 6 # catalyst, 7 # catalyst, and 8 # catalyst.

Example 3

The concentration of phenyltrimethylammonium chloride was changed to 0.05 mol/L, 0.1 mol/L, 0.3 mol/L, and 1 mol/L respectively. All the rest preparation procedures were the same as those in Example 1 to correspondingly prepare 9 # catalyst, 10 # catalyst, 11 # catalyst, and 12 # catalyst.

Example 4

The oxalic acid was replaced with hydrochloric acid, nitric acid, sulfuric acid, acetic acid, citric acid, and an equimolar mixture of the described acids, respectively. All the rest preparation procedures were the same as those in Example 1 to correspondingly prepare 13 # catalyst, 14 # catalyst, 15 # catalyst, 16 # catalyst, 17 # catalyst and 18 # catalyst.

Example 5

The dry air atmosphere was changed to an air atmosphere with a steam concentration of 10%, an air atmosphere with a steam concentration of 40%, and an atmosphere with a steam concentration of 100%, respectively. All the rest preparation procedures were the same as those in Example 1 to correspondingly prepare 19 # catalyst, 20 # catalyst, and 21 # catalyst.

Example 6

The dry air atmosphere was changed to an air atmosphere with a steam concentration of 20%, the corresponding temperature was changed to 350° C., 500° C., 600° C., 750° C., 800° C., 300° C., respectively. All the rest preparation procedures were the same as those in Example 1 to correspondingly prepare 22 # catalyst, 23 # catalyst, 24 # catalyst, 25 # catalyst, 26 # catalyst and 27 # catalyst.

Example 7

After Na-MOR was treated in phenyltrimethylammonium chloride aqueous solution, it was subjected to the following separate treatment respectively: (1) treatment in oxalic acid aqueous solution; (2) calcination treatment in dry air; (3) treatment in the air atmosphere with a steam concentration of 10%, wherein the particular treatment conditions were the same as those of the corresponding treatment in Example 1. Then, the resulting samples were treated by an ammonium nitrate aqueous solution respectively, and the conditions thereof were also the same as those of in Example 1. Finally, the 28 # catalyst, 29 # catalyst, and 30 # catalyst were obtained.

Example 8

The silicon to aluminum atomic ratio of the Na-MOR was changed to 6.5, 10, 20, 30, 50 respectively. All the rest preparation procedures were the same as those in Example 1 to correspondingly prepare 31 # catalyst, 32 # catalyst, 33 # catalyst, 34 # catalyst, and 35 # catalyst.

Example 9

The treatment temperature in the phenyltrimethylammonium chloride solution was changed to 20° C., 60° C. and 100° C. respectively. All the rest preparation procedures were the same as those in Example 1 to correspondingly prepare 36 # catalyst, 37 # catalyst and 38 # catalyst.

The treatment time in the phenyltrimethylammonium chloride solution was changed to 1 hour, 2 hours, 6 hours, and 10 hours respectively. All the rest preparation procedures were the same as those in Example 1 to correspondingly prepare 39 # catalyst, 40 # catalyst, 41 # catalyst and 42 # catalyst.

The number of times the treatment in the phenyltrimethylammonium chloride solution was changed to 2 and 8 respectively. All the rest preparation procedures were the same as those in Example 1 to correspondingly prepare 43 # catalyst and 44 # catalyst.

Example 10

The temperature of the acid treatment was changed to 30° C., 80° C. and 100° C. respectively. All the rest preparation procedures were the same as those in Example 1 to correspondingly prepare 45 # catalyst, 46 # catalyst and 47 # catalyst.

The time of the acid treatment was changed to 1 hour, 2 hours, 8 hours, and 10 hours respectively. All the rest preparation procedures were the same as those in Example 1 to correspondingly prepare 48 # catalyst, 49 # catalyst, 50 # catalyst and 51 # catalyst.

The number of times the acid treatment was changed to 2 and 10 respectively. All the rest preparation procedures were the same as those in Example 1 to correspondingly prepare 52 # catalyst and 53 # catalyst.

Example 11

The treatment time in the dry air atmosphere was changed to 1 hour, 2 hours, 6 hours, and 10 hours respectively. All the rest preparation procedures were the same as those in Example 1 to correspondingly prepare 54 # catalyst, 55 # catalyst, 56 # catalyst and 57 # catalyst.

Example 12

The treatment temperature in the ammonium nitrate aqueous solution was changed to 20° C., 30° C., 90° C., and 100° C. respectively. All the rest preparation procedures were the same as those in Example 1 to correspondingly prepare 58 # catalyst, 59 # catalyst, 60 # catalyst and 61 # catalyst.

The treatment time in the ammonium nitrate aqueous solution was changed to 1 hour, 2 hours, 6 hours, and 10 hours respectively. All the rest preparation procedures were the same as those in Example 1 to correspondingly prepare 62 # catalyst, 63 # catalyst, 64 # catalyst and 65 # catalyst.

Example 13

The calcination time was changed to 2 hours, 6 hours, and 8 hours respectively. All the rest preparation procedures were the same as those in Example 1 to correspondingly prepare 66 # catalyst, 67 # catalyst and 68 # catalyst.

The calcination temperature was changed to 300° C., 400° C., 750° C., and 800° C. respectively. All the rest preparation procedures were the same as those in Example 1 to correspondingly prepare 69 # catalyst, 70 # catalyst, 71 # catalyst and 72 # catalyst.

Example 14

The ammonium nitrate aqueous solution was replaced with an ammonium chloride aqueous solution, an ammonium sulfate aqueous solution, and an ammonium acetate aqueous solution, respectively. All the rest preparation procedures were the same as those in Example 1 to correspondingly prepare 73 # catalyst, 74 # catalyst and 75 # catalyst.

Example 15

The catalytic performance of the above-mentioned catalyst was investigated under the following conditions.

10 g catalyst was loaded into a fixed bed reactor with inner diameter of 28 mm, in which the temperature was raised to 550° C. at a rate of 5° C./min under a nitrogen atmosphere, and was maintained 4 hours. Then the temperature was lowered to 220° C. under the nitrogen atmosphere. The pressure in the reaction system was increased to 5 MPa by using CO. The reaction raw materials were passed through the catalyst bed from top to bottom. The space velocity of the feeding dimethyl ether was 1.50 $h^{-1}$. The molar ratio of carbon monoxide to dimethyl ether was 2:1, and the feeding gas containing carbon monoxide does not comprise other gases. Under the reaction temperature was 220° C. and the catalytic reaction ran 100 hours, the reaction results were shown in Table 1.

TABLE 1

Reaction results of different catalysts for carbonylation of dimethyl ether

| Catalyst | Conversion rate of dimethyl ether (%) | CO Conversion rate (%) | Selectivity of methyl acetate (%) | Selectivity of other product (%) | Space-time yield of methyl acetate (gMAc/ (gcat · h)) |
|---|---|---|---|---|---|
| 1# | 71.5 | 35.8 | 99.9 | 0.1 | 1.72 |
| 2# | 47.3 | 23.7 | 99.8 | 0.2 | 1.14 |
| 3# | 52.1 | 26.1 | 99.5 | 0.5 | 1.25 |
| 4# | 54.5 | 27.3 | 99.3 | 0.7 | 1.31 |
| 5# | 57.5 | 28.8 | 99.6 | 0.4 | 1.38 |
| 6# | 56.9 | 28.5 | 99.5 | 0.5 | 1.37 |
| 7# | 75.9 | 38.0 | 99.6 | 0.4 | 1.82 |
| 8# | 79.3 | 40.0 | 99.5 | 0.5 | 1.90 |
| 9# | 24.2 | 12.1 | 92.6 | 7.4 | 0.54 |
| 10# | 80.8 | 40.4 | 94.5 | 5.5 | 1.84 |
| 11# | 80.9 | 40.5 | 99.9 | 0.1 | 1.95 |
| 12# | 81.8 | 40.9 | 99.9 | 0.1 | 1.97 |
| 13# | 68.5 | 34.3 | 98.3 | 1.7 | 1.62 |
| 14# | 70.8 | 35.4 | 98.4 | 1.6 | 1.68 |
| 15# | 52.1 | 26.1 | 97.5 | 2.5 | 1.23 |
| 16# | 75.6 | 37.8 | 98.8 | 1.2 | 1.80 |
| 17# | 63.8 | 31.9 | 90.8 | 9.2 | 1.40 |
| 18# | 73.5 | 36.8 | 98.9 | 1.1 | 1.75 |
| 19# | 75.8 | 37.8 | 94.5 | 5.5 | 1.73 |
| 20# | 82.9 | 41.4 | 99.9 | 0.1 | 2.00 |
| 21# | 41.8 | 20.9 | 99.9 | 0.1 | 1.01 |
| 22# | 0.8 | 0.4 | 91.3 | 8.7 | 0.02 |
| 23# | 2.3 | 1.2 | 92.3 | 7.7 | 0.05 |
| 24# | 32.9 | 16.5 | 95.8 | 4.2 | 0.76 |
| 25# | 62.8 | 31.4 | 98.6 | 1.4 | 1.49 |
| 26# | 36.8 | 18.4 | 91.9 | 8.1 | 0.82 |
| 27# | 16.8 | 8.4 | 91.9 | 8.1 | 0.37 |
| 28# | 63.5 | 31.8 | 99.9 | 0.1 | 1.53 |
| 29# | 47.5 | 23.8 | 99.9 | 0.1 | 1.15 |
| 30# | 62.5 | 31.2 | 99.9 | 0.1 | 1.51 |
| 31# | 36.8 | 18.4 | 98.7 | 1.3 | 0.88 |
| 32# | 49.3 | 24.7 | 99.3 | 0.7 | 1.18 |
| 33# | 62.3 | 31.5 | 99.4 | 0.6 | 1.49 |
| 34# | 45.9 | 23.0 | 99.1 | 0.9 | 1.10 |
| 35# | 35.9 | 18.0 | 99.1 | 0.9 | 0.86 |
| 36# | 68.5 | 35.8 | 99.9 | 0.1 | 1.65 |
| 37# | 69.5 | 34.8 | 99.4 | 0.6 | 1.67 |
| 38# | 57.8 | 28.9 | 99.1 | 0.9 | 1.38 |
| 39# | 71.2 | 35.6 | 99.1 | 0.9 | 1.70 |
| 40# | 71.3 | 35.7 | 99.9 | 0.1 | 1.72 |

TABLE 1-continued

Reaction results of different catalysts for carbonylation of dimethyl ether

| Catalyst | Conversion rate of dimethyl ether (%) | CO Conversion rate (%) | Selectivity of methyl acetate (%) | Selectivity of other product (%) | Space-time yield of methyl acetate (gMAc/(gcat·h)) |
|---|---|---|---|---|---|
| 41# | 71.4 | 35.7 | 99.4 | 0.6 | 1.71 |
| 42# | 71.6 | 35.8 | 99.1 | 0.9 | 1.71 |
| 43# | 48.4 | 24.2 | 99.1 | 0.9 | 1.16 |
| 44# | 76.8 | 38.4 | 99.9 | 0.1 | 1.85 |
| 45# | 68.9 | 34.5 | 99.4 | 0.6 | 1.65 |
| 46# | 68.9 | 34.5 | 99.1 | 0.9 | 1.65 |
| 47# | 37.8 | 18.9 | 99.1 | 0.9 | 0.90 |
| 48# | 66.5 | 33.3 | 99.9 | 0.1 | 1.60 |
| 49# | 67.8 | 33.9 | 99.4 | 0.6 | 1.63 |
| 50# | 56.8 | 28.4 | 99.1 | 0.9 | 1.36 |
| 51# | 32.8 | 16.4 | 99.1 | 0.9 | 0.78 |
| 52# | 68.7 | 34.4 | 99.9 | 0.1 | 1.66 |
| 53# | 56.8 | 28.4 | 99.4 | 0.6 | 1.36 |
| 54# | 61.3 | 30.7 | 99.1 | 0.9 | 1.47 |
| 55# | 63.8 | 31.9 | 99.1 | 0.9 | 1.53 |
| 56# | 66.8 | 33.4 | 99.9 | 0.1 | 1.61 |
| 57# | 45.9 | 23.0 | 99.4 | 0.6 | 1.10 |
| 58# | 71.3 | 35.7 | 99.1 | 0.9 | 1.71 |
| 59# | 71.5 | 35.8 | 99.1 | 0.9 | 1.71 |
| 60# | 71.6 | 35.8 | 99.9 | 0.1 | 1.73 |
| 61# | 71.8 | 35.9 | 99.4 | 0.6 | 1.72 |
| 62# | 71.6 | 35.8 | 99.1 | 0.9 | 1.71 |
| 63# | 71.5 | 35.8 | 99.1 | 0.9 | 1.71 |
| 64# | 71.5 | 35.8 | 99.9 | 0.1 | 1.72 |
| 65# | 71.6 | 35.8 | 99.4 | 0.6 | 1.72 |
| 66# | 34.5 | 17.3 | 99.1 | 0.9 | 0.83 |
| 67# | 71.3 | 35.7 | 99.1 | 0.9 | 1.71 |
| 68# | 71.3 | 35.7 | 99.9 | 0.1 | 1.72 |
| 69# | 5.6 | 2.8 | 99.4 | 0.6 | 0.13 |
| 70# | 24.5 | 12.3 | 99.1 | 0.9 | 0.59 |
| 71# | 10.2 | 5.1 | 99.1 | 0.9 | 0.24 |
| 72# | 1.8 | 0.9 | 99.9 | 0.1 | 0.04 |
| 73# | 70.5 | 35.3 | 99.9 | 0.1 | 1.70 |
| 74# | 51.5 | 25.5 | 99.9 | 0.1 | 1.24 |
| 75# | 74.5 | 37.2 | 99.9 | 0.1 | 1.79 |

Through the evaluation of the catalyst performance in the reaction system, it can be found that the side reaction activity can be selectively eliminated by the technical solution. A catalyst with high activity and high stability can be obtained without using pyridine pre-adsorption which would cause poisoning.

Example 16

Reaction Results of Carbonylation of Dimethyl Ether at Different Reaction Temperatures 10 g 1 # catalyst was loaded into the fixed-bed reactor with an inner diameter of 28 mm. The temperature was raised to 550° C. at a rate of 5° C./min under a nitrogen atmosphere, and was maintained for 4 hours. Then, the temperature was lowered to the reaction temperature under the nitrogen atmosphere. The pressure in the reaction system was increased to 5 MPa by using CO. The reaction raw materials were passed through the catalyst bed from top to bottom. The weight hourly space velocity of the feeding dimethyl ether was 1.50 h$^{-1}$. The molar ratio of carbon monoxide to dimethyl ether was 1:1, and the feeding gas containing carbon monoxide does not comprise other gases. The reaction temperature was 170° C., 200° C., 230° C., 240° C. and 260° C. respectively. The reaction results of the catalytic reaction running for 100 hours were shown in Table 2.

TABLE 2

Reaction results at different reaction temperatures

| | The temperature at the inlet of the reactor | | | | |
|---|---|---|---|---|---|
| | 170 | 200 | 230 | 240 | 260 |
| Conversion rate of dimethyl ether (%) | 15.7 | 42.1 | 76.0 | 87.8 | 95.8 |
| CO conversion rate (%) | 15.7 | 42.1 | 76.0 | 87.8 | 95.8 |
| Selectivity of methyl acetate (%) | 97.8 | 99.7 | 99.5 | 99.1 | 96.3 |
| Selectivity of other product (%) | 2.2 | 0.3 | 0.5 | 0.9 | 3.7 |

Example 17

Reaction Results of the Carbonylation of Dimethyl Ether Under Different Reaction Pressures 1 # catalyst was used in this example. The reaction pressures were 1, 6, 10, and 15 MPa, the reaction temperature was 220° C. and other conditions were the same as those in Example 16. Under the reaction ran for 100 hours, the reaction results were shown in Table 3.

TABLE 3

Reaction results under different reaction pressures

| | Reaction Pressure (MPa) | | | |
|---|---|---|---|---|
| | 1 | 6 | 10 | 15 |
| Conversion rate of dimethyl ether (%) | 18.3 | 59.3 | 62.8 | 72.3 |
| CO conversion rate (%) | 18.3 | 59.3 | 62.8 | 72.3 |
| Selectivity of methyl acetate (%) | 98.7 | 99.9 | 99.9 | 99.9 |
| Selectivity of other product (%) | 1.3 | 0.1 | 0.1 | 0.1 |

Example 18

Reaction Results of the Carbonylation of Dimethyl Ether at Different Space Velocities of Dimethyl Ether.

1 # catalyst was used in this example. The weight hourly space velocities of the feeding dimethyl ether were 0.35 h$^{-1}$, 1 h$^{-1}$, 2.5 h$^{-1}$ and 4 h$^{-1}$ respectively, the reaction temperature was 200° C., and other conditions were the same as those in Example 15. Under the reaction ran for 100 hours, the reaction results were shown in Table 4.

TABLE 4

Reaction results under different space velocities of dimethyl ether

| | Space velocity of the feeding dimethyl ether (h$^{-1}$) | | | |
|---|---|---|---|---|
| | 0.35 | 1 | 2.5 | 4 |
| Conversion rate of dimethyl ether (%) | 92.5 | 63.39 | 25.26 | 14.8 |
| CO conversion rate (%) | 92.5 | 63.39 | 25.26 | 14.8 |
| Selectivity of methyl acetate (%) | 99.9 | 99.8 | 99.2 | 98.7 |
| Selectivity of other product (%) | 0.1 | 0.2 | 0.8 | 1.3 |

Example 19

Reaction Results of Carbonylation of Dimethyl Ether Under Different Molar Ratios of Carbon Monoxide to Dimethyl Ether.

1 # catalyst was used in this example. The weight hourly space velocity of the feeding dimethyl ether was 1.5 h$^{-1}$, and the molar ratios of carbon monoxide to dimethyl ether were 0.2:1, 0.5:1, 2:1, 4:1, 8:1 and 12:1 respectively. The reaction temperature was 210° C., and other conditions were the same as those in Example 16. Under the reaction ran for 100 hours, the reaction results were shown in Table 5.

TABLE 5

Reaction results under different molar ratios of carbon monoxide to dimethyl ether

| | Molar ratio of carbon monoxide to dimethyl ether | | | | | |
|---|---|---|---|---|---|---|
| | 12:1 | 8:1 | 4:1 | 2:1 | 0.5:1 | 0.2:1 |
| Conversion rate of carbon monoxide (%) | 8.13 | 10.7 | 18.45 | 32.9 | 90.6 | 97.5 |
| Conversion rate of dimethyl ether (%) | 97.5 | 85.6 | 73.8 | 65.8 | 45.32 | 19.5 |
| Selectivity of methyl acetate (%) | 97.8 | 98.1 | 99.5 | 99.4 | 99.3 | 99.3 |

Example 20

Reaction Results of Carbonylation of Dimethyl Ether Under the Feeding Gas Containing Carbon Monoxide Comprises Inert Gas.

23 # catalyst was used in this example. The weight hourly space velocity of the feeding dimethyl ether was 0.5 $h^{-1}$. The feeding gas containing carbon monoxide comprises inactive gas, the molar ratio of the feeding gas containing carbon monoxide to dimethyl ether was 4:1, the reaction temperature was 225° C., and other conditions were the same as those in Example 16. Under the reaction ran for 4000 hours the reaction results were shown in Table 6.

TABLE 6

Reaction results under the feeding gas containing carbon monoxide comprises inert gas

| Feeding gas containing carbon monoxide | | Conversion rate of dimethyl ether (%) | Conversion rate of carbon monoxide (%) | Selectivity of methyl acetate (%) |
|---|---|---|---|---|
| Volume content of inactive gas (%) | Volume content of CO (%) | | | |
| 85 ($N_2$) | 15 | 40.0 | 88.9 | 99.8 |
| 70 ($N_2$) | 30 | 75.2 | 92.8 | 99.8 |
| 20 ($N_2$) | 80 | 86.3 | 35.5 | 99.7 |
| 0 | 100 | 98.5 | 28.3 | 99.2 |
| 28($N_2$) + 3($CO_2$) + 5(Ar) + 8($H_2$) | 56 | 82.7 | 51.5 | 99.5 |

The above examples are only illustrative, and do not limit the present application in any form. Any change or modification, made by the skilled in the art based on the technical content disclosed above, without departing from the spirit of the present application, is equivalent example and falls within the scope of the present application.

The invention claimed is:

1. A method for preparing a molecular sieve catalyst, wherein the method comprises following steps:
   (1) subjecting a Na-MOR molecular sieve to the organic ammonium salt exchange to obtain a precursor I;
   (2) subjecting the precursor I to an acid treatment to obtain a precursor II;
   (3) subjecting the precursor II to a calcination treatment to obtain a precursor III;
   (4) subjecting the precursor III to the ammonium ion exchange to obtain a precursor IV; and
   (5) calcining the precursor IV to obtain the molecular sieve catalyst;
   wherein the organic ammonium salt exchange is an alkyl ammonium halide salt exchange and the alkyl ammonium halide salt is at least one of compounds having a chemical formula shown in Formula I,

Formula I wherein $R^1$, $R^2$ and $R^3$ are independently selected from $C_1$~$C_{10}$ alkyl group;
   $R^4$ is selected from one of $C_1$ to $C_{10}$ alkyl group and $C_6$ to $C_{10}$ aryl group; and
   X is selected from at least one of F, Cl, Br and I;
   a silicon to aluminum atomic ratio of the Na-MOR molecular sieve ranges from 6 to 50;
   wherein the calcination treatment in step (3) is carried out in an atmosphere with a steam concentration ranging from 0 to 100%, at a temperature ranging from 300 to 800° C. for a time ranging from 1 to 10 hours.

2. The method for preparing the molecular sieve catalyst according to claim 1, wherein the organic ammonium salt exchange in step (1) is carried out by placing the Na-MOR molecular sieve in an organic ammonium salt solution at a temperature ranging from 20 to 100° C. for a time ranging from 1 to 10 hours;
   a concentration of the organic ammonium salt solution ranges from 0.05 to 1 mol/L; and
   the number of times the organic ammonium salt exchange is conducted ranges from 2 to 8; and conditions for the organic ammonium salt exchange refers to a temperature ranging from 30 to 80° C., and a time ranging from 2 to 6 hours.

3. The method for preparing the molecular sieve catalyst according to claim 1, wherein an acid used in the acid treatment in step (2) is at least one of hydrochloric acid, nitric acid, sulfuric acid, acetic acid, oxalic acid and citric acid; and
   the acid treatment in step (2) is carried out in an acidic solution at a temperature ranging 30 to 100° C. for a time ranging from 1 to 10 hours.

4. The method for preparing the molecular sieve catalyst according to claim 3, wherein the number of times the acid treatment is conducted ranges from 2 to 10; and the acid treatment is carried out in the acidic solution at a temperature ranging 30 to 80° C. for a time ranging from 2 to 8 hours.

5. The method for preparing the molecular sieve catalyst according to claim 1, wherein the calcination treatment in step (3) is carried out in an atmosphere with a steam concentration ranging from 0 to 100%, at a temperature ranging from 350 to 750° C. for a time ranging from 2 to 6 hours.

6. The method for preparing the molecular sieve catalyst according to claim 1, wherein the ammonium ion exchange in step (4) is carried out at a temperature ranging from 20 to 100° C. for a time ranging from 1 to 10 hours.

7. The method for preparing the molecular sieve catalyst according to claim 6, wherein,
- the number of times ammonium ion exchange is conducted ranges from 2 to 5;
- the ammonium ion exchange is carried out at a temperature ranging from 30 to 90° C. for a time ranging from 2 to 6 hours; and
- the ammonium ion exchange is carried out in an ammonium ion-containing solution, and the ammonium ion-containing solution is at least one of ammonium nitrate solution, ammonium chloride solution, ammonium sulfate solution, and ammonium acetate solution.

8. The method for preparing the molecular sieve catalyst according to claim 1, wherein the calcination treatment in step (5) is carried out in an air atmosphere at a temperature ranging from 300 to 800° C. for a time ranging 2 to 8 hours.

9. The method for preparing the molecular sieve catalyst according to claim 1, wherein the method comprises following steps:
- a) subjecting a solid containing Na-MOR molecular sieve to an exchange treatment in an alkyl ammonium halide salt solution at a temperature ranging from 20 to 100° C. for a time ranging from 1 to 10 hours to obtain the precursor I, wherein the number of times the exchange treatment is conducted ranges from 2 to 8;
- b) treating the precursor I with an acidic solution at a temperature ranging from 30 to 100° C. for a time ranging from 1 to 10 hours to obtain the precursor II, wherein the number of times the treatment with the acidic solution is conducted ranges from 2 to 10;
- c) treating the precursor II in an atmosphere with a steam concentration ranging from 0% to 100%, at a temperature ranging from 300 to 800° C. for a time ranging from 1 to 10 hours to obtain the precursor III;
- d) subjecting the precursor III to an exchange treatment in an ammonium nitrate aqueous solution at a temperature ranging from 20 to 100° C. for a time ranging from 1 to 10 hours to obtain the precursor IV, wherein the number of times the exchange treatment is conducted ranges from 2 to 5 times; and
- e) calcining the precursor IV in an air atmosphere at a temperature ranging from 300 to 800° C. for a time ranging 2 to 8 hours to obtain the molecular sieve catalyst.

10. A method for producing methyl acetate by carbonylation of dimethyl ether comprising feeding dimethyl ether and a feeding gas containing carbon monoxide into a reactor equipped with a catalyst bed to contact with a catalyst to produce methyl acetate;
- wherein, the catalyst is the molecular sieve catalyst prepared by the method according to claim 1.

11. The method for producing methyl acetate by carbonylation of dimethyl ether according to claim 10, wherein reaction conditions of the carbonylation of dimethyl ether include the following:
- a reaction temperature ranges from 150 to 280° C., a reaction pressure ranges from 0.5 to 25.0 MPa, and a weight hourly space velocity of dimethyl ether ranges from 0.05 to 5 $h^{-1}$; and
- a molar ratio of carbon monoxide to dimethyl ether ranges from 0.1:1 to 30:1.

12. The method for producing methyl acetate by carbonylation of dimethyl ether according to claim 11, wherein the reaction conditions of the carbonylation of dimethyl ether include the following:
- the reaction temperature ranges from 160 to 280° C., the reaction pressure ranges from 0.5 to 20.0 MPa, and the weight hourly space velocity of dimethyl ether ranges from 0.2 to 4.0 $h^{-1}$; and
- the molar ratio of carbon monoxide to dimethyl ether ranges from 0.1:1 to 20:1.

13. The method for producing methyl acetate by carbonylation of dimethyl ether according to claim 10, wherein the feeding gas containing carbon monoxide comprises from 15% to 100% carbon monoxide by volume; and
- the feeding gas containing carbon monoxide further comprises at least one of hydrogen, nitrogen, helium, argon, carbon dioxide, methane and ethane.

14. The method for preparing a molecular sieve catalyst according to claim 1, wherein $R^1$, $R^2$ and $R^3$ in Formula I are independently selected from $CH_3-$, $CH_3CH_2-$, $CH_3(CH_2)_nCH_2-$, $(CH_3)_2CH-$, $(CH_3)_2CHCH_2-$ or $CH_3CH_2(CH_3)CH-$;
$R^4$ is $CH_3-$, $CH_3-$, $CH_3CH_2-$, $CH_3(CH_2)_mCH_2-$, $(CH_3)_2CH-$, $(CH_3)_2CHCH_2-$, $CH_3CH_2(CH_3)CH-$, $C_6H_5-$, $CH_3C_6H_4-$, $(CH_3)_2C_6H_3-$ or $C_6H_5CH_2-$;
wherein, n and m are independently selected from 1, 2, 3 or 4.

15. The method for preparing a molecular sieve catalyst according to claim 1, wherein the calcination treatment in step (5) is carried out in the air atmosphere at a temperature ranging from 400 to 750° C. for a time ranging 4 to 6 hours.

16. The method for producing methyl acetate by carbonylation of dimethyl ether according to claim 11, wherein the reaction conditions of carbonylation of dimethyl ether contain the followings:
- the reaction temperature ranges from 170 to 260° C., the reaction pressure ranges from 1.0 to 15.0 MPa, and the weight hourly space velocity of dimethyl ether ranges from 0.1 to 4.0 $h^{-1}$; and
- the molar ratio of carbon monoxide to dimethyl ether ranges from 0.2:1 to 15:1.

* * * * *